United States Patent
Zhang et al.

(10) Patent No.: US 11,220,631 B2
(45) Date of Patent: Jan. 11, 2022

(54) METHOD OF MAKING BIOMASS FLUORESCENT CARBON QUANTUM DOTS FROM SOYBEAN DREGS BY HYDROTHERMAL SYNTHESIS AND USES THEREOF

(71) Applicant: Zhejiang University of Science & Technology, Zhejiang (CN)

(72) Inventors: Liting Zhang, Zhejiang (CN);
Shengdao Shan, Zhejiang (CN);
Changai Zhang, Zhejiang (CN);
Wanpeng Liu, Zhejiang (CN); Haifeng Zhuang, Zhejiang (CN); Yongpeng Luo, Zhejiang (CN); Zhichao Hu, Zhejiang (CN)

(73) Assignee: Zhejiang University of Science & Technology, Hangzhou (CN)

( * ) Notice: Subject to any disclaimer, the term of this patent is extended or adjusted under 35 U.S.C. 154(b) by 48 days.

(21) Appl. No.: 16/833,539

(22) Filed: Mar. 28, 2020

(65) Prior Publication Data
US 2020/0392404 A1    Dec. 17, 2020

(30) Foreign Application Priority Data

Jun. 12, 2019   (CN) ......................... 201910504487.X

(51) Int. Cl.
*C09K 11/65*   (2006.01)
*C01B 32/15*   (2017.01)
(Continued)

(52) U.S. Cl.
CPC .............. *C09K 11/65* (2013.01); *C01B 32/15* (2017.08); *G01N 21/6428* (2013.01);
(Continued)

(58) Field of Classification Search
CPC .... C09K 11/65; C01B 32/15; G01N 21/6428; G01N 33/1886; G01N 2021/7786;
(Continued)

(56) References Cited

U.S. PATENT DOCUMENTS

2018/0312752 A1    11/2018 Liu et al.

FOREIGN PATENT DOCUMENTS

| CN | 102745669 A | * 10/2012 |
| CN | 104355301 | 2/2015 |

(Continued)

OTHER PUBLICATIONS

Zhu et al., "Bifunctional fluorescent carbon nanodots: green synthesis via soy milk and application as metal-free electrocatalysts for oxygen reduction", 2012, Chemical Communications, 48,9367-9369 (Year: 2012).*

(Continued)

*Primary Examiner* — Samuel P Siefke
*Assistant Examiner* — Henry H Nguyen

(57) ABSTRACT

Disclosed is a method of preparing a carbon quantum dot from soybean dregs by hydrothermal synthesis, including: mixing the soybean dregs with water, and subjecting the reaction mixture under heating at 100-500° C. in an autoclave for reaction; cooling the reaction mixture when the reaction is completed, and removing insoluble substances from the reaction mixture; and dialyzing the reaction mixture, and lyophilizing the dialyzed product to produce the carbon quantum dot. The invention further provides the carbon quantum dot prepared by the above method and a use thereof in the detection of $Fe^{3+}$ and $Hg^{2+}$ in water, where the lowest detection limit can reach 30 nmol/L and the detection range is 0.1-50 μmol/L.

1 Claim, 8 Drawing Sheets

(51) Int. Cl.
  *G01N 21/64* (2006.01)
  *G01N 33/18* (2006.01)
  *B82Y 15/00* (2011.01)
  *B82Y 20/00* (2011.01)
  *B82Y 40/00* (2011.01)
  *G01N 21/77* (2006.01)

(52) U.S. Cl.
  CPC .......... *G01N 33/1886* (2013.01); *B82Y 15/00* (2013.01); *B82Y 20/00* (2013.01); *B82Y 40/00* (2013.01); *G01N 2021/6432* (2013.01); *G01N 2021/7786* (2013.01)

(58) Field of Classification Search
  CPC ............ G01N 2021/6432; B82Y 15/00; B82Y 20/00; B82Y 40/00; B82Y 30/00
  See application file for complete search history.

(56) References Cited

FOREIGN PATENT DOCUMENTS

| | | | | | |
|---|---|---|---|---|---|
| CN | 108456519 | A | * | 8/2018 | |
| CN | 109095453 | | | 12/2018 | |
| KR | 101403534 | B1 | * | 6/2014 | ............ B82Y 40/00 |

OTHER PUBLICATIONS

Jia et al., "Highly luminescent N-doped carbon dots from black soya beans for free radical scavenging, Fe3+ sensing and cellular imaging", Dec. 2018,Spectrochemica Acta Part A, 211,363-372 (Year: 2018).*

Zhu et al., Electronic Supplementary Information (ESI), "Bifunctional fluorescent carbon nanodots: green synthesis via soy milk and application as metal-free electrocatalysts for oxygen reduction", 2012, Chemical Communications, 48,9367-9369 (Year: 2012).*

Translation of CN 108456519A, Guo, Yan-zhu, Aug. 28, 2018 (Year: 2018).*

Translation of CN102745669A, Liu, Chang-Jun, Oct. 24, 2012 (Year: 2012).*

Translation of KR101403534B1, Moon, Byoung Gi, Jun. 3, 2014 (Year: 2014).*

* cited by examiner

METHOD OF MAKING BIOMASS FLUORESCENT CARBON QUANTUM DOTS FROM SOYBEAN DREGS BY HYDROTHERMAL SYNTHESIS AND USES THEREOF

CROSS-REFERENCE TO RELATED APPLICATIONS

This application claims the benefit of priority from Chinese Patent Application No. 201910504487.X, filed on Jun. 12, 2019. The content of the aforementioned application, including any intervening amendments thereto, is incorporated herein by reference in its entirety.

TECHNICAL FIELD

This application relates to waste biomass recycle and environmental monitoring, and more particularly to a method of making carbon quantum dots from soybean dregs by hydrothermal synthesis and uses thereof.

BACKGROUND OF THE INVENTION

As a novel carbon nanomaterial, carbon quantum dots have the characteristics of good water solubility, high luminous intensity, low biological toxicity, desirable biocompatibility, strong chemical stability and readily-modifiable surface, so that they are expected to replace traditional semiconductor quantum dots and toxic organic dyes. Moreover, the green synthesis of carbon quantum dots from biological materials is in accordance with the requirements of chemical development and the concept of atom economy, receiving considerable attention.

Currently, there are several methods for preparing carbon quantum dots, mainly including electrochemical method, oxidation with strong acid, arc-discharge method, laser ablation, chemical oxidation, combustion method and template method. However, due to the defects of complicated process and high cost, these methods are not suitable for the industrial production of fluorescent carbon quantum dots. Therefore, it is of great significance to develop a simple and environmentally-friendly method to prepare the carbon quantum dots.

At present, the carbon quantum dots are generally synthesized from various chemicals and biomass. It has been recently reported that the fluorescent carbon quantum dots can be greenly prepared not only from chemicals such as polyethylene glycol, vitamin C, ethanol and gelatin, but also from biomass materials such as apple juice, strawberry juice, corn flour and potatoes. However, it has not been reported with regard to the use of hydrothermal treatment to prepare the fluorescent carbon quantum dots from waste soybean dregs. In addition, the carbon quantum dots currently prepared from biomass are free of response to the heavy metal ions such as $Fe^{3+}$.

SUMMARY OF THE INVENTION

An object of the invention is to provide a green method of preparing fluorescent carbon quantum dots, where the prepared carbon quantum dots have good storage stability and excellent pH stability, and are suitable for the rapid detection of heavy metal ions in water such as $Fe^{3+}$ and $Hg^{2+}$.

The technical solutions of the invention are described as follows.

In a first aspect, the invention provides a biomass fluorescent carbon quantum dot, wherein the carbon quantum dot comprises C, N and O, and a molar ratio of C to N to O is 60-80:5-15:10-30. It has been demonstrated by testing that in the fluorescent carbon quantum dot, the carbon element mainly exists in 5 forms including: C—C, C—N, C—O, C=N/C=O and O—C=O; the oxygen element mainly exists in 2 forms including: C=O and HO—C/C—O—C; and the nitrogen element mainly exists in 3 forms including: C—N—C, C—C=N and N—H.

In a second aspect, the invention provides a method of preparing the above fluorescent carbon quantum dot from soybean dregs by hydrothermal synthesis, comprising:

mixing the soybean dregs with water, and subjecting the reaction mixture under heating at 100-500° C. in an autoclave for reaction;

cooling the reaction mixture when the reaction is completed, and removing insoluble substances from the reaction mixture; and dialyzing the reaction mixture, and lyophilizing the dialyzed product to produce the carbon quantum dot.

In an embodiment, the reaction is performed under magnetic or mechanical stirring at a rate of 50-1000 rpm.

In an embodiment, the method comprises:

(1) mixing the soybean dregs with water in a mass ratio of 1:1-10, wherein the soybean dregs is derived from the preparation of a soybean milk;

(2) reacting the reaction mixture in an autoclave under magnetic stirring at 100-500° C. and 200 rpm for 1-24 h; and (3) naturally cooling the reaction mixture; removing the insoluble substances by filtration or centrifugation; dialyzing the reaction mixture; and lyophilizing the dialyzed product to produce the carbon quantum dot.

In an embodiment, in step (2), the reaction is performed at 150° C.-300° C. for 3-15 h, preferably at 200° C.-300° C. for 3-12 h, and more preferably at 250° C.-300° C. for 3-5 h, which can lead to a relatively higher yield of the carbon quantum dot.

In an embodiment, in step (2), the reaction is performed at 200° C. for 3 h, which leads to a significantly-improved yield of the carbon quantum dot.

In an embodiment, in step (2), the autoclave is stainless.

In a third aspect, the invention further provides a use of the carbon quantum dot, comprising:

applying the carbon quantum dot to the detection of $Fe^{3+}$ and/or $Hg^{2+}$ in water.

In an embodiment, a concentration of the $Fe^{3+}$ or $Hg^{2+}$ in the water is 0.01 μmol/L or more, preferably 0.01-100 μmol/L or diluted to 0.01-100 μmol/L, and more preferably 0.1-50 μmol/L or diluted to 0.1-50 μmol/L.

In an embodiment, the concentration of the $Fe^{3+}$ or $Hg^{2+}$ in the water is 0.03-50 μmol/L or diluted to 0.03-50 μmol/L.

In an embodiment, the concentration of $Hg^{2+}$ in the water is 0.1-50 μmol/L or diluted to 0.1-50 μmol/L, and the concentration of $Fe^{3+}$ in the water is 10-50 μmol/L or diluted to 10-50 μmol/L. In these ranges, $Hg^{2+}$ and $Fe^{3+}$ respectively show a linear relationship with the relative fluorescence intensity of the carbon quantum dots, which makes the detection easier.

Compared to the prior art, the invention has the following beneficial effects.

The photoluminescent carbon quantum dots prepared herein have a particle size of 10-20 nm and have a good solubility and dispersibility in water, which can be used as a fluorescent probe in the detection of $Hg^{2+}$ and $Fe^{3+}$ in water. The detection method involving the use of the carbon quantum dots has a lowest detection limit of 30 nmol/L and a detection range of 0.1-50 μmol/L. In addition, the preparation method of the invention involves readily-available raw materials, simple operation and equipment, low cost and high yield, facilitating the industrial production.

BRIEF DESCRIPTION OF THE DRAWINGS

FIG. 6A shows the element composition of the carbon quantum dot; FIG. 6B shows the existing forms of C in the carbon quantum dot; FIG. 6C shows the existing forms of O in the carbon quantum dot; and FIG. 6D shows the existing forms of N in the carbon quantum dot.

DETAILED DESCRIPTION OF EMBODIMENTS

Determination of fluorescent carbon quantum dots and calculation of relative quantum yield are described as follows.

In the determination, quinine sulfate with a quantum yield of 54% is used as a reference standard. First, aqueous solutions of the fluorescent carbon quantum dots and the quinine sulfate are respectively measured for the absorbance at the same excitation wavelength. Then the fluorescence emission peaks of the two solutions are respectively measured at the excitation wavelength, and integrated to obtain areas of the fluorescence peaks. Finally, the results obtained above are substituted into the following equation to calculate the relative quantum yield:

$$Q_{BCDs} = Q_{ref} \cdot \frac{I_{BCDs}}{I_{ref}} \cdot \frac{A_{ref}}{A_{BCDs}} \cdot \frac{\eta_{BCDs}^2}{\eta_{ref}^2},$$

where $Q_{BCDS}$ and $Q_{ref}$ respectively refer to the quantum yields of the sample and the reference standard (quinine sulfate has a quantum yield of 0.54); $I_{BCDS}$ and $I_{ref}$ respectively refer to the emission intensities of the sample and the reference standard; $A_{BCDS}$ and $A_{ref}$ respectively refer to the absorbances of the sample and the reference standard at the excitation wavelength; and $\eta_{BCDS}$ and $\eta_{ref}$ respectively refer to refractive indexes of the sample and the reference standard (the refractive index of water is 1.33).

Example 1

(1) Fresh soybean dregs derived from the preparation of soybean milk was mixed uniformly with ultrapure water in a mass ratio of 1:4.

(2) 60 mL of the reaction mixture obtained in step (1) was transferred to a 100 mL stainless autoclave and heated at 200° C. under magnetic stirring at 200 rpm for 3 h.

(3) The reaction mixture was naturally cooled to room temperature and filtered or centrifuged to remove insoluble substances. Then the resulting filtrate or supernatant was dialyzed in a 1000 Da dialysis bag and lyophilized at −50° C. to give 50 mg of a carbon quantum dot (3.7% quantum yield).

Figure 1:
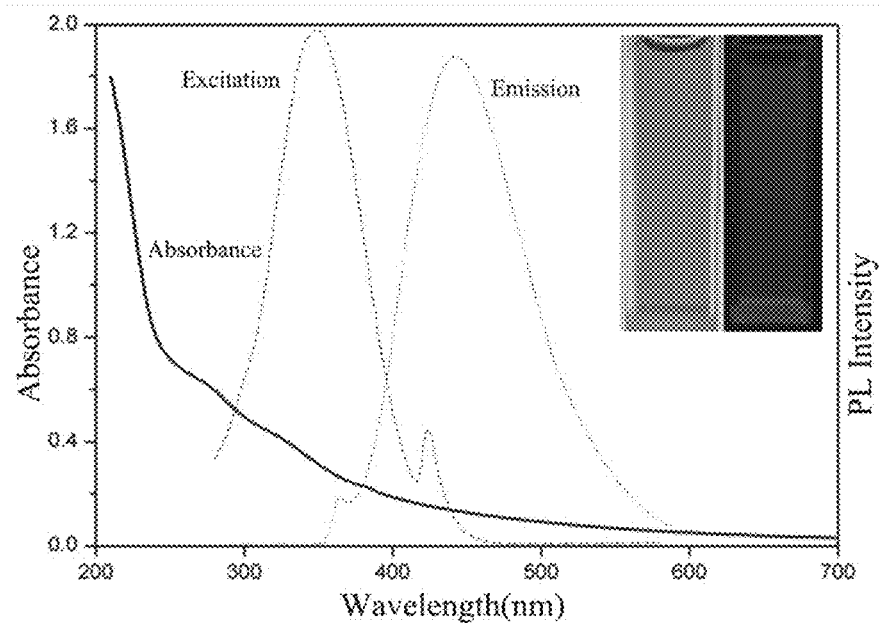
FIG. 1 shows an ultraviolet-visible absorption spectrum, an ultraviolet excitation spectrum and an emission spectrum of a solution of a carbon quantum dot prepared in Example 1 of the invention.

FIG. 1 showed an ultraviolet-visible absorption spectrum, an ultraviolet excitation spectrum and an emission spectrum of a solution of the carbon quantum dot prepared herein, where the carbon quantum dot was observed to have significant absorption in the ultraviolet range of 210-400 nm, a maximum excitation wavelength of 346 nm and a maximum emission wavelength of 440 nm.

Figure 2:
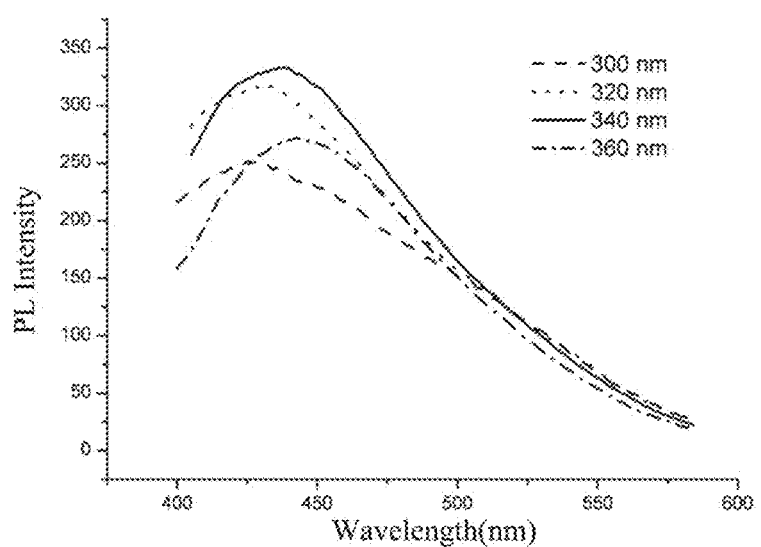
FIG. 2 shows an emission spectrum of the solution of the carbon quantum dot prepared in Example 1 of the invention at different excitation wavelengths.

FIG. 2 showed an emission spectrum of the solution of the carbon quantum dot prepared herein at different excitation wavelengths. It can be seen that the intensity of the transmitted wave was gradually enhanced with the increase of the excitation wavelength, while in the range of higher than 340 nm, the intensity of the transmitted wave was negatively correlated with the excitation wavelength, which indicated that the maximum excitation wavelength was near 340 nm and the result was consistent with that shown in FIG. 1.

Figure 3:
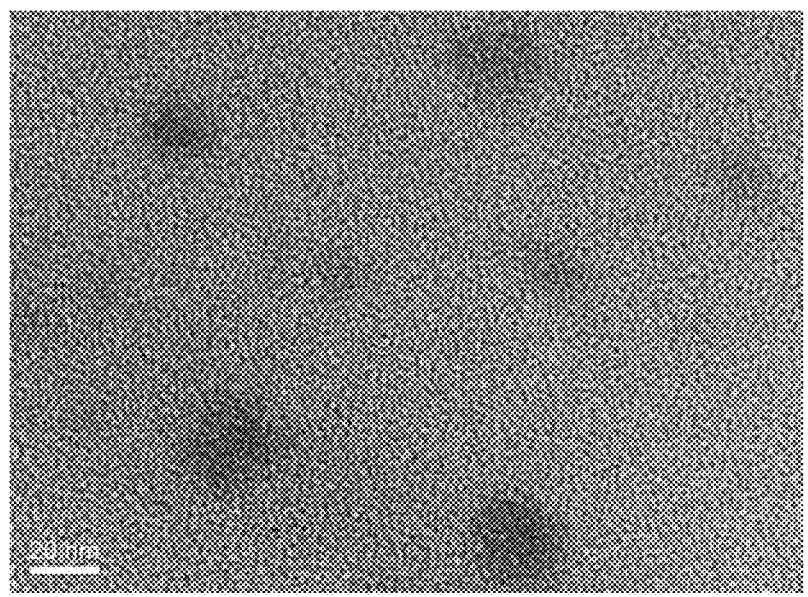
FIG. 3 is a TEM of the carbon quantum dot prepared in Example 1 of the invention.

FIG. 3 was a TEM of the carbon quantum dot prepared herein, where the carbon quantum dot had a particle size of 10-20 nm.

Figure 4:
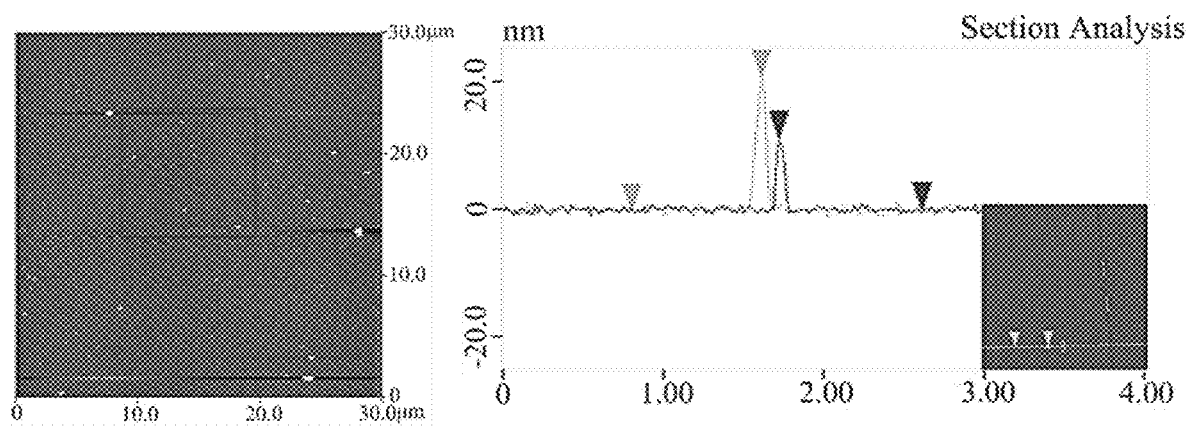
FIG. 4 is an AFM of the carbon quantum dot prepared in Example 1 of the invention.

FIG. 4 was an AFM of the carbon quantum dot prepared herein, where the carbon quantum dot had a height of 11-20 nm, which was consistent with the result shown in FIG. 3.

Figure 5:
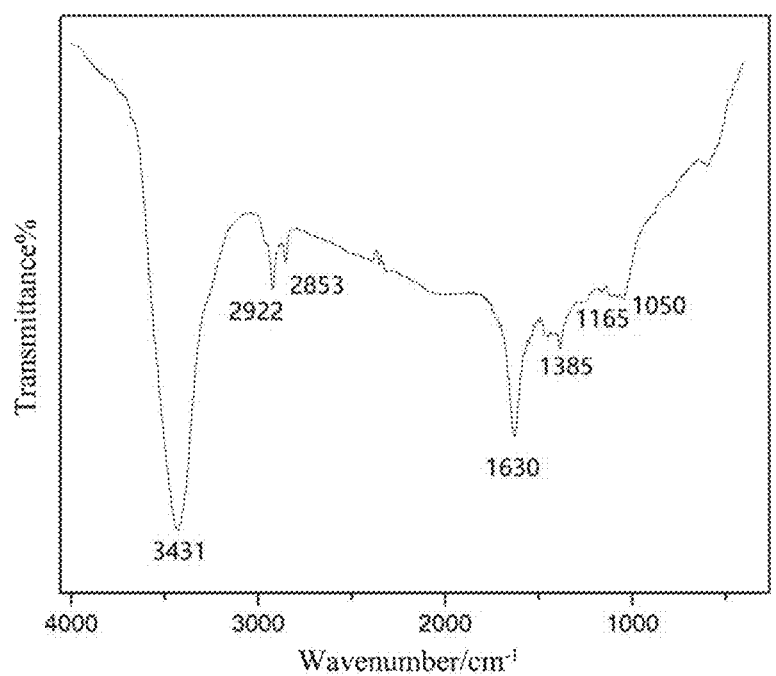
FIG. 5 shows a FTIR spectrum of the carbon quantum dot prepared in Example 1 of the invention.

FIG. 5 was a FTIR spectrum of the carbon quantum dot prepared herein. It can be observed that the carbon quantum dot has a stretching vibration of OH/NH at 3431 $cm^{-1}$, a stretching vibration of CH at 2853-2922 $cm^{-1}$ and a stretching vibration of C=O/C=C at 1630 $cm^{-1}$, and the spectrum between 1050 $cm^{-1}$ and 1385 $cm^{-1}$ demonstrated the presence of a large number of C—O bonds.

Figure 6A:
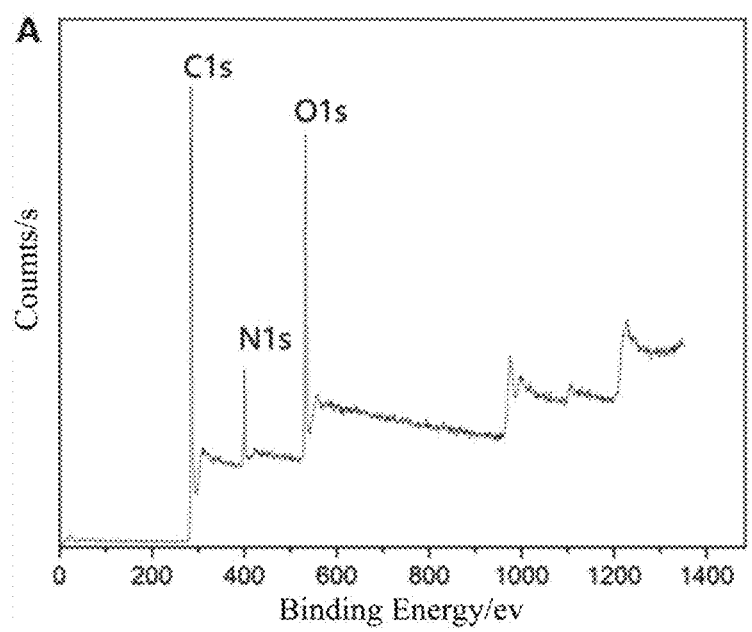
FIGS. 6A-6D are XPS patterns of the carbon quantum dot prepared in Example 1 of the invention, where
Figure 6B:
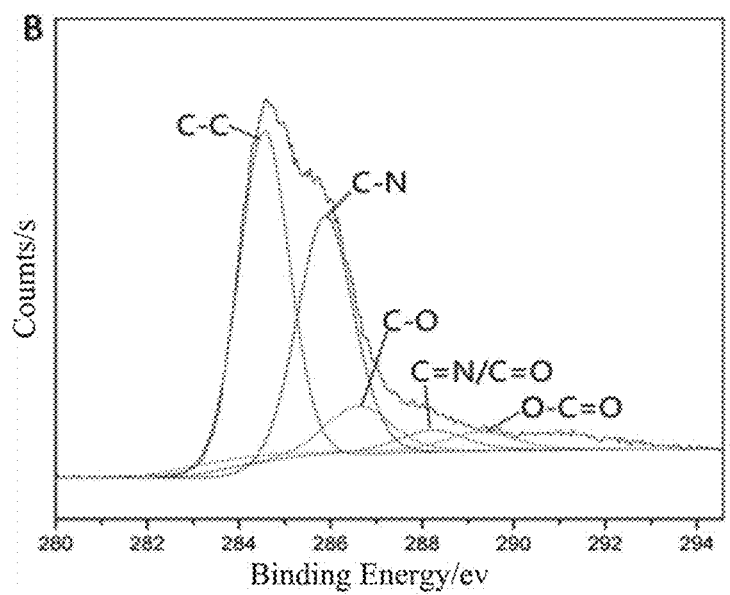
Figure 6C:
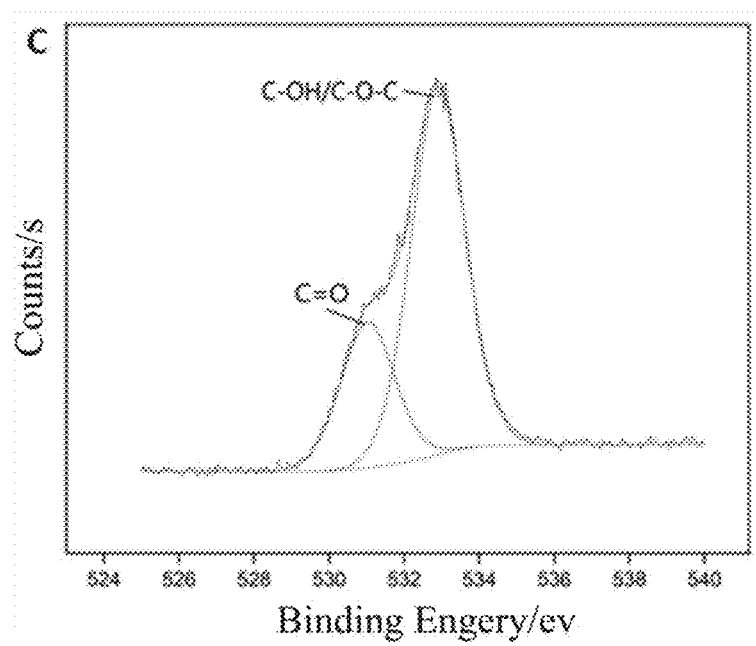
Figure 6D:
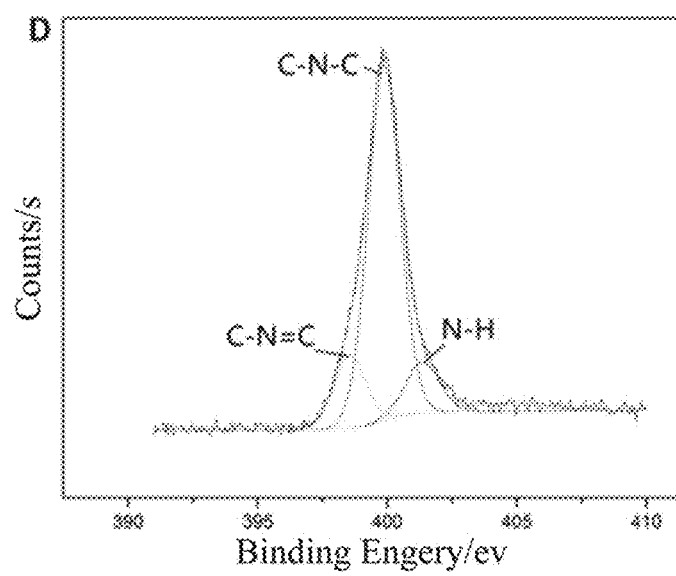

FIGS. 6A-6D were XPS patterns of the carbon quantum dot prepared herein. As shown in FIG. 6A, the carbon quantum dot was mainly composed of C, N and O in a ratio approximately of 72.8:8.8:19.1. As shown in FIG. 6B, there were about 5 forms of C in the carbon quantum dot, including C—C, C—N, C—O, C=N/C=O and O—C=O. As shown in FIG. 6C, there were about 2 forms of O in the carbon quantum dot, including C=O and HO—C/C—O—C. As shown in FIG. 6D, there were about 3 forms of N in the carbon quantum dot, including C—N—C, C—C=N and N—H.

Figure 7:
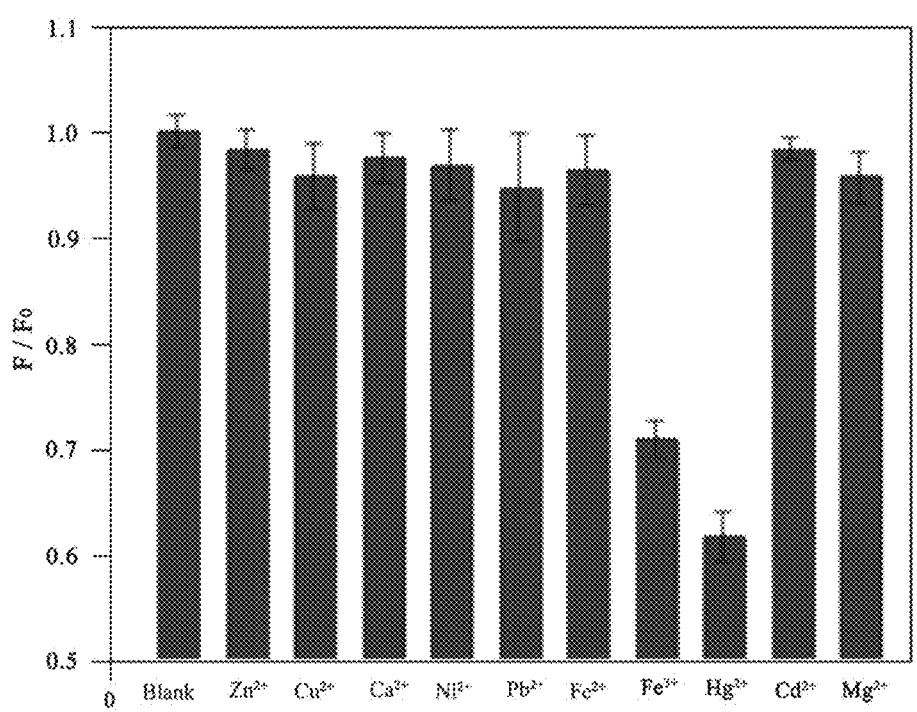
FIG. 7 shows the effect of various metal ions on relative fluorescence intensity ($F/F_0$) of the carbon quantum dot prepared in Example 1 of the invention.

FIG. 7 showed the effect of various metal ions on relative fluorescence intensity ($F/F_0$) of the carbon quantum dot prepared herein, where the system contained 2.9 mL of a solution of 40 μmol/L metal ions in ultrapure water (pH 7.0) and 0.1 mL of a 5 mg/L carbon quantum dot solution. It can be concluded from FIG. 7 that the carbon quantum dot prepared herein showed significant responses respectively to $Hg^{2+}$ and $Fe^{3+}$.

Figure 8A:
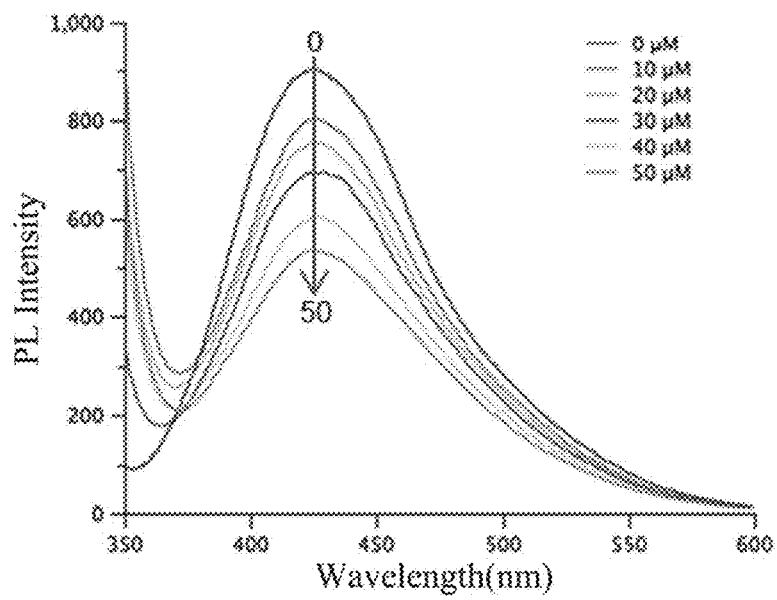
FIGS. 8A-8B show the effect of $Hg^{2+}$ level on the intensity of the emission spectrum of the carbon quantum dot prepared in Example 1 of the invention.
Figure 8B:
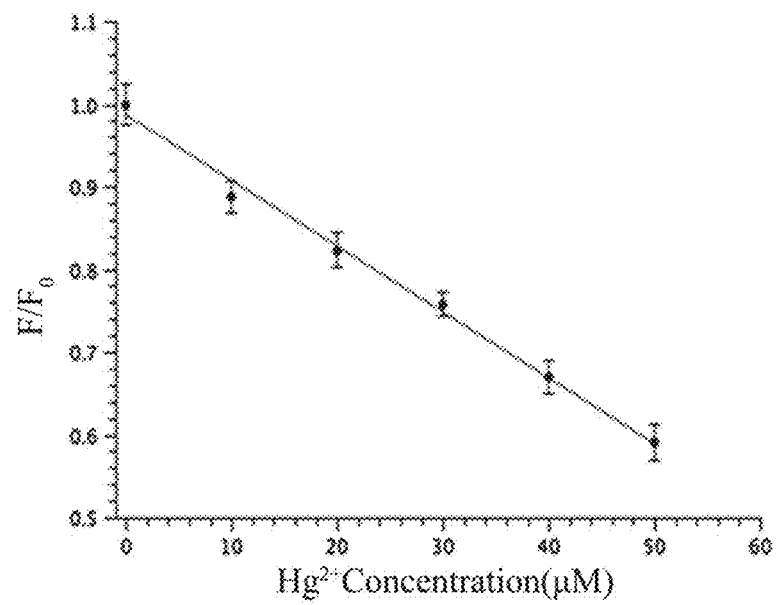
Figure 8C:
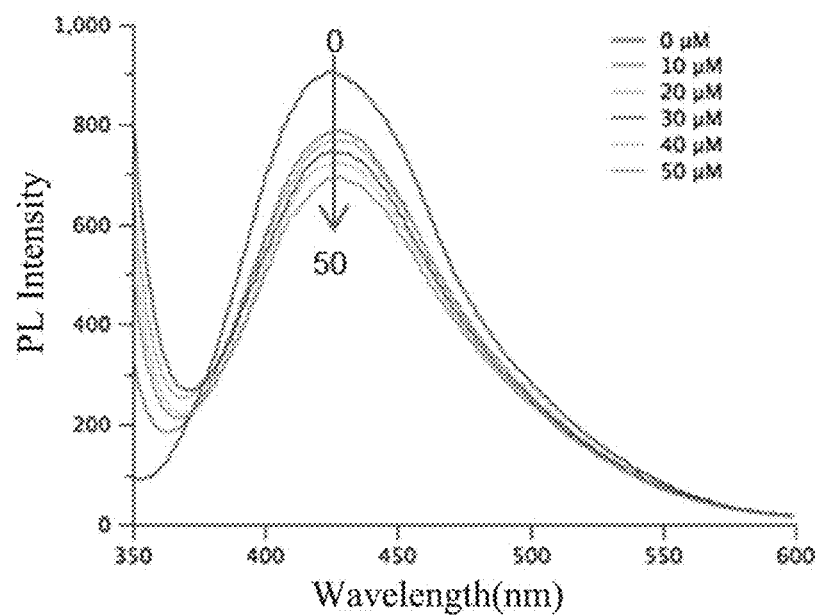
FIGS. 8C-8D show the effect of $Fe^{3+}$ level on the intensity of the emission spectrum of the carbon quantum dot prepared in Example 1 of the invention.
Figure 8D:
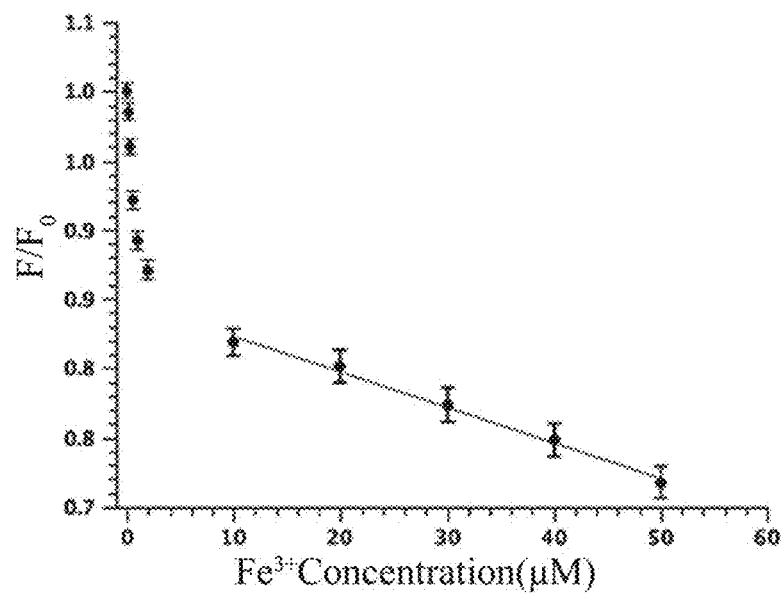

FIGS. 8A-8B showed the effect of $Hg^{2+}$ level on the intensity of the emission spectrum of the carbon quantum dot prepared herein, and FIGS. 8C-8D show the effect of $Fe^{3+}$ level on the intensity of the emission spectrum of the carbon quantum dot. As shown in FIGS. 8A-8B, in the case of a content of 0.01-50 μmol/L, $Hg^{2+}$ showed remarkable fluorescence-quenching effect on the carbon quantum dot prepared herein, and the quenching efficiency had a good negative linear relationship with the $Hg^{2+}$ content. Similarly, a good negative linear relationship was also observed in FIGS. 8C-8D between $Fe^{3+}$ content and the quenching efficiency in the presence of 0.01-50 μmol/L of $Fe^{3+}$. In a low concentration range of metal ions such as 0-1 μmol/L, the carbon quantum dot showed more sensitive response to the metal ions, but the relationship therebetween was not linear. Therefore, in actual detection, the sample in the desired concentration range can be calibrated to obtain the relationship between the spectrum intensity and the concentration through linear fitting. Based on this relationship, the concentrations of $Fe^{3+}$ and $Hg^{2+}$ in water can be directly detected.

Example 2

(1) Fresh soybean dregs derived from the preparation of soybean milk was mixed uniformly with ultrapure water in a mass ratio of 1:2.

(2) 60 mL of the reaction mixture obtained in step (1) was transferred to a 100 mL stainless autoclave and heated at 300° C. under magnetic stirring at 200 rpm for 3 h.

(3) The reaction mixture was naturally cooled to room temperature and filtered or centrifuged to remove insoluble substances. Then the resulting filtrate or supernatant was dialyzed in a 1000 Da dialysis bag and lyophilized at −50° C. to give 110 mg of a carbon quantum dot (4.7% quantum yield).

Example 3

(1) Fresh soybean dregs derived from the preparation of soybean milk was mixed uniformly with ultrapure water in a mass ratio of 1:4.

(2) 60 mL of the reaction mixture obtained in step (1) was transferred to a 200 mL polytetrafluoroethylene high-temperature reactor and heated at 250° C. for 5 h.

(3) The reaction mixture was naturally cooled to room temperature and filtered or centrifuged to remove insoluble substances. Then the resulting filtrate or supernatant was dialyzed in a 1000 Da dialysis bag and lyophilized at −50° C. to give 50 mg of a carbon quantum dot (4.2% quantum yield).

Example 4

(1) Fresh soybean dregs derived from the preparation of soybean milk was mixed uniformly with ultrapure water in a mass ratio of 1:8.

(2) 60 mL of the reaction mixture obtained in step (1) was transferred to a 100 mL stainless autoclave and heated at 200° C. for 12 h.

(3) The reaction mixture was naturally cooled to room temperature and filtered or centrifuged to remove insoluble substances. Then the resulting filtrate or supernatant was dialyzed in a 1000 Da dialysis bag and lyophilized at −50° C. to give 20 mg of a carbon quantum dot (3.5% quantum yield).

Application

Water samples, collected from Xianlin Reservoir (Yuhang district, Hanzhou), were filtered with a 0.22 μm aqueous membrane, and then respectively added with 0.5 μmol/L, 1.0 μmol/L and 5.0 μmol/L of $Hg^{2+}$ and 0.1 μmol/L, 5.0 μmol/L and 10 μmol/L of $Fe^{3+}$. With the carbon quantum dots prepared by the method according to the present invention, individual water samples were measured in terms of metal ions based on the standard curves respectively in FIG. 8B and FIG. 8D (i.e., the linear portion). It can be seen in Table 1 that the method of the invention had a recovery rate of 90%-103.8% for all of the samples except the sample added with 0.1 μmol/L of $Fe^{3+}$. Therefore, this method can ensure a reliable detection for $Hg^{2+}$ in the range of 0.01-50 μmol/L and $Fe^{3+}$ in the range of 10-50 μmol/L.

TABLE 1

Recovery rates of the method in the detection of $Hg^{2+}$ and $Fe^{3+}$ in samples

| | Sample ID | Addition amount (μM) | Detecting value (μM) | Recovery (%) |
|---|---|---|---|---|
| $Hg^{2+}$ | NO. 1 | 0.5 | 0.45 | 90 |
| | NO. 2 | 1.0 | 0.96 | 96 |
| | NO. 3 | 5.0 | 5.19 | 103.8 |
| $Fe^{3+}$ | NO. 4 | 0.1 | 0.04 | 40 |
| | NO. 5 | 5.0 | 4.52 | 90.4 |
| | NO. 6 | 10.0 | 9.53 | 95.3 |

Described above are merely preferred embodiments of the invention, and they are not intended to limit the invention. Various variations and modifications made by those skilled in the art without departing from the spirit of the invention should fall within the scope defined by the appended claims.

What is claimed is:

1. A method of using a carbon quantum dot prepared from soybean dregs by hydrothermal synthesis, comprising:
   mixing the soybean dregs with water to obtain a mixture, and placing the mixture in an autoclave followed by heating at 100-300° C. for 1-24 h for reaction;
   cooling the mixture when the reaction is completed, and removing insoluble substances from the mixture;
   dialyzing the mixture, and lyophilizing the dialyzed product to produce the carbon quantum dot; and
   detecting $Fe^{3+}$ and/or $Hg^{2+}$ in the water using the carbon quantum dot as a fluorescent probe;
   wherein a mass ratio of the soybean dregs to the water is 1:1-10; and the reaction is performed under mechanical or magnetic stirring at a rate of 50-1000 rpm;
   the carbon quantum dot comprises C, N and O, and a molar ratio of C to N to O is 60-80:5-15:10-30; and
   a concentration of the $Fe^{3+}$ or the $Hg^{2+}$ in the water is 0.1-50 μmol/L.

* * * * *